United States Patent
Lopez et al.

(10) Patent No.: US 9,931,497 B2
(45) Date of Patent: Apr. 3, 2018

(54) MEDICAL CONNECTOR

(71) Applicant: CAIR L.G.L., Lissieu (FR)

(72) Inventors: Georges Antoine Lopez, Ecully (FR); Patrick Delorme, Chaponost (FR)

(73) Assignee: CAIR L.G.L., Lissieu (FR)

( * ) Notice: Subject to any disclaimer, the term of this patent is extended or adjusted under 35 U.S.C. 154(b) by 89 days.

(21) Appl. No.: 14/652,612

(22) PCT Filed: Jan. 28, 2014

(86) PCT No.: PCT/FR2014/050153
§ 371 (c)(1),
(2) Date: Jun. 16, 2015

(87) PCT Pub. No.: WO2014/118462
PCT Pub. Date: Aug. 7, 2014

(65) Prior Publication Data
US 2016/0001057 A1  Jan. 7, 2016

(30) Foreign Application Priority Data

Jan. 31, 2013 (FR) ..................... 13 50836

(51) Int. Cl.
*A61M 39/10* (2006.01)
*A61M 39/26* (2006.01)

(52) U.S. Cl.
CPC ............ *A61M 39/10* (2013.01); *A61M 39/26* (2013.01)

(58) Field of Classification Search
CPC ............................... A61M 39/10; A61M 39/26
See application file for complete search history.

(56) References Cited

U.S. PATENT DOCUMENTS

2008/0103482 A1 * 5/2008 Fangrow ............... A61M 39/10
604/523
2008/0249508 A1  10/2008 Lopez et al.

FOREIGN PATENT DOCUMENTS

| EP | 0798013 A1 | 10/1997 |
| EP | 1890760 A1 | 2/2008 |
| FR | 2894150 A1 | 6/2007 |
| WO | WO-2006/013433 A1 | 2/2006 |
| WO | WO-2008/052140 A2 | 5/2008 |

OTHER PUBLICATIONS

International Search Report for PCT/FR2014/050153, dated Apr. 8, 2014.

\* cited by examiner

*Primary Examiner* — Bradley J Osinski
(74) *Attorney, Agent, or Firm* — Marshall, Gerstein & Borun LLP

(57) ABSTRACT

A male luer medical connector includes a needle having a distal portion with a hole opening and contained in the cavity of a resilient seal. The needle has, apart from its distal portion, an additional hole. The seal and needle are shaped so that when the connector is connected, the compressed seal forms with the needle, immediately upstream of the upper level of the additional hole, a sealed cavity for receiving by way of passage in the additional hole a part of the fluid contained in the needle; and when the seal is released the cavity contains fluid when the lateral hole opening into the needle is sealed, and the portions of the seal, downstream and upstream of the cavity respectively, as well as the additional hole, are shaped so the downstream portion closes a lateral hole while the same cavity continues to discharge the fluid into the needle.

13 Claims, 8 Drawing Sheets

FIG.2
FIG.3
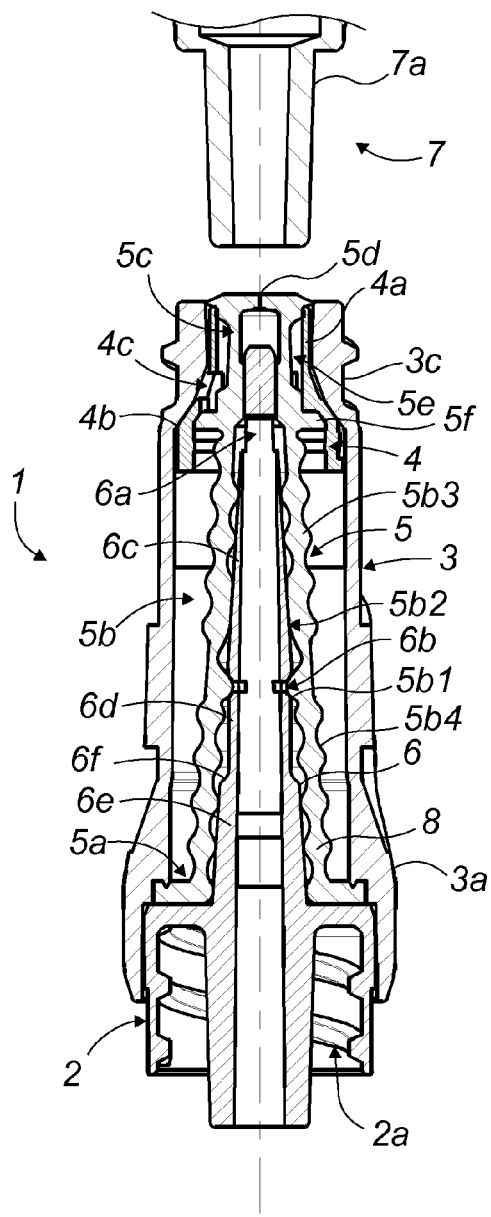
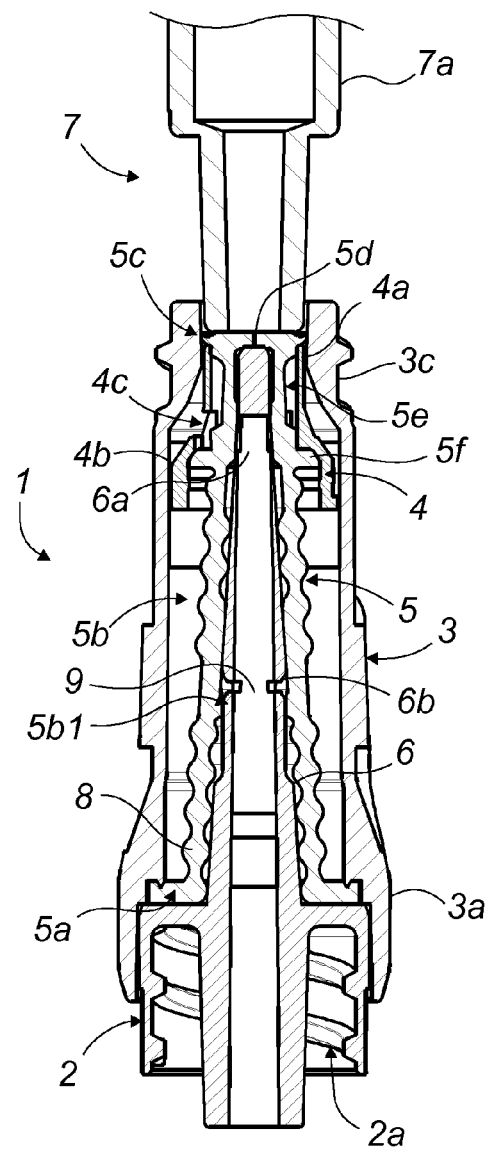

FIG.4
FIG.5
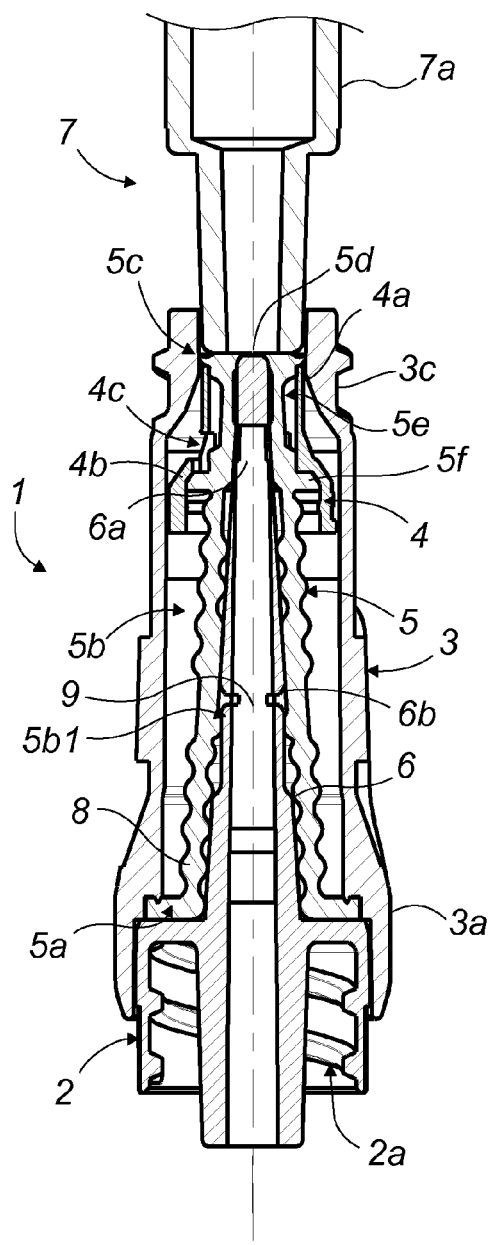
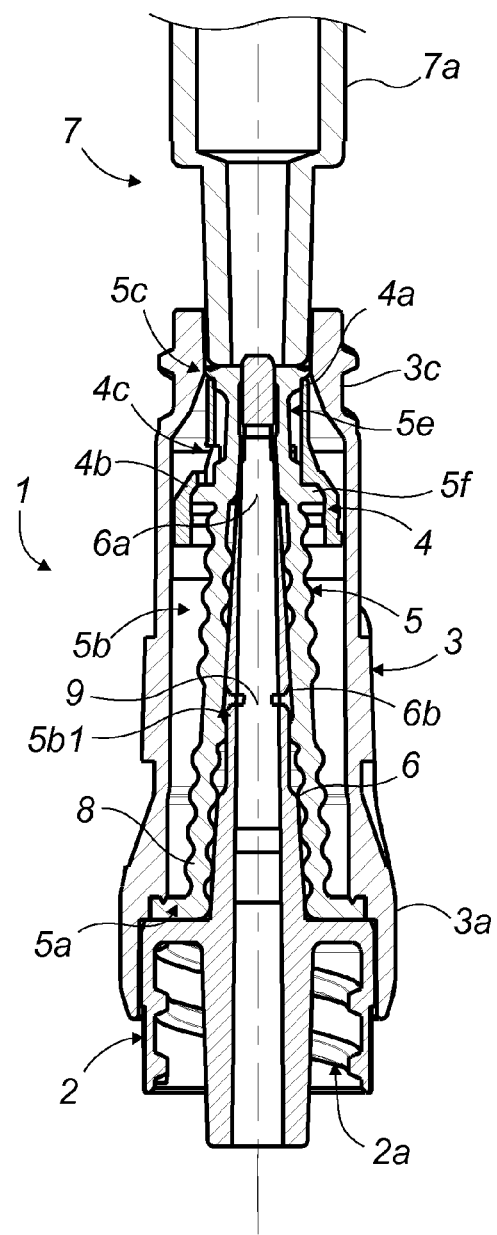

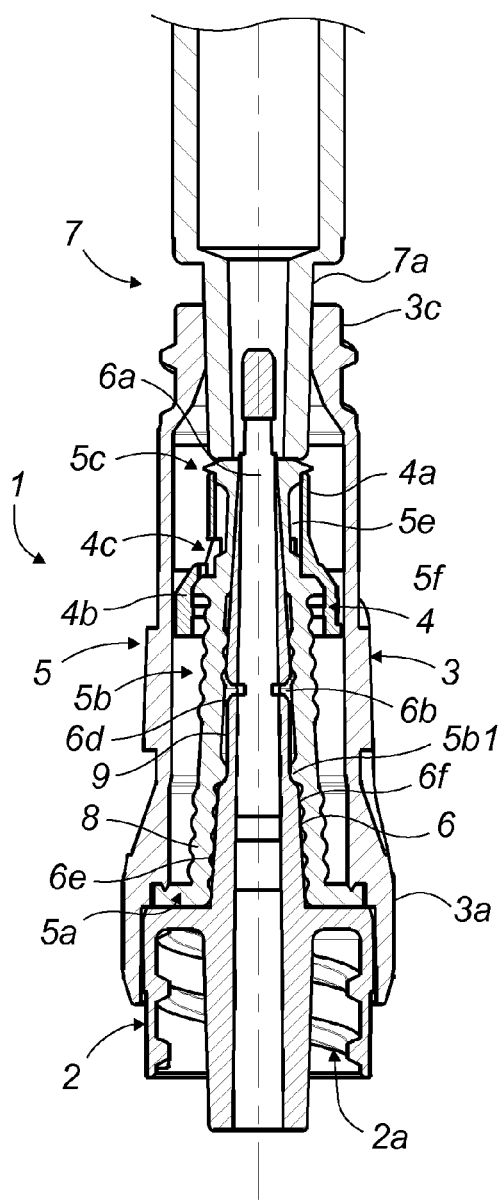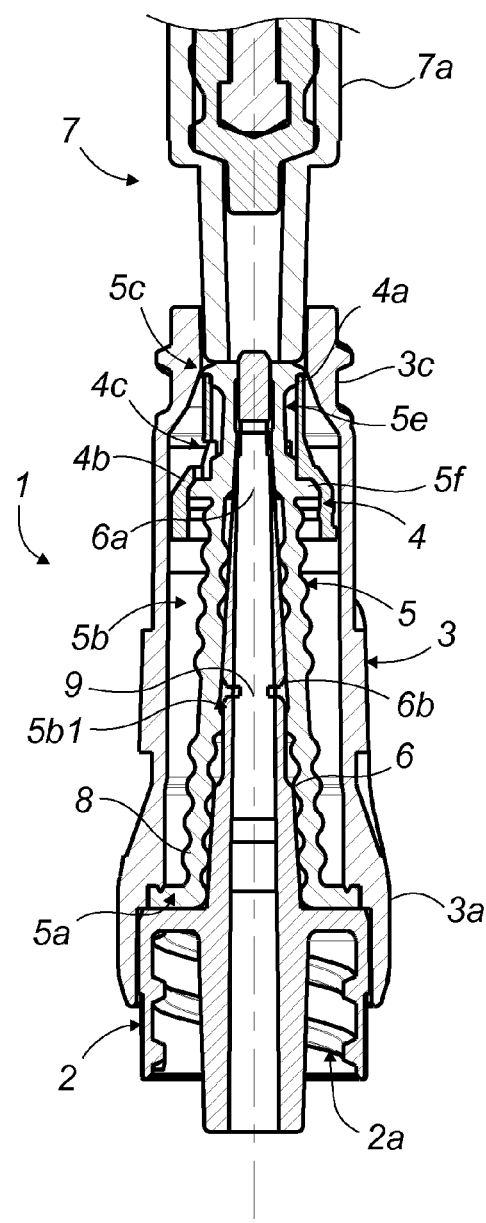

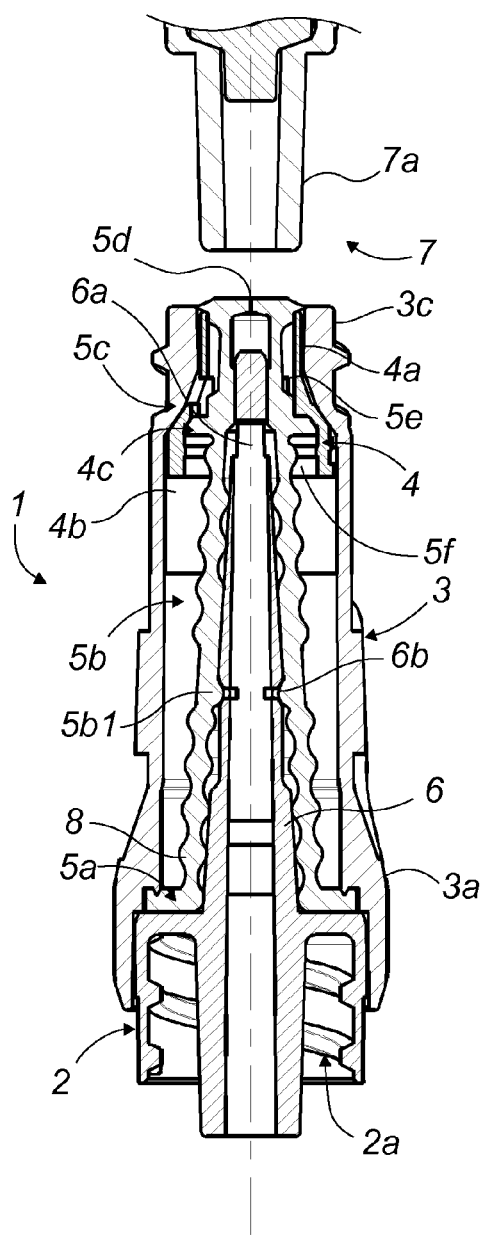
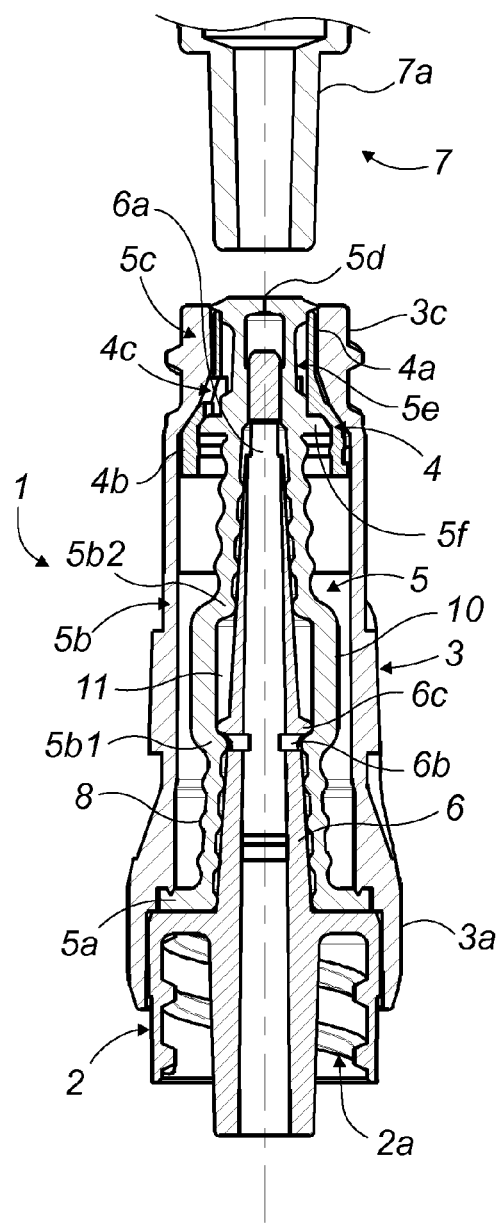

*FIG.14* *FIG.15*
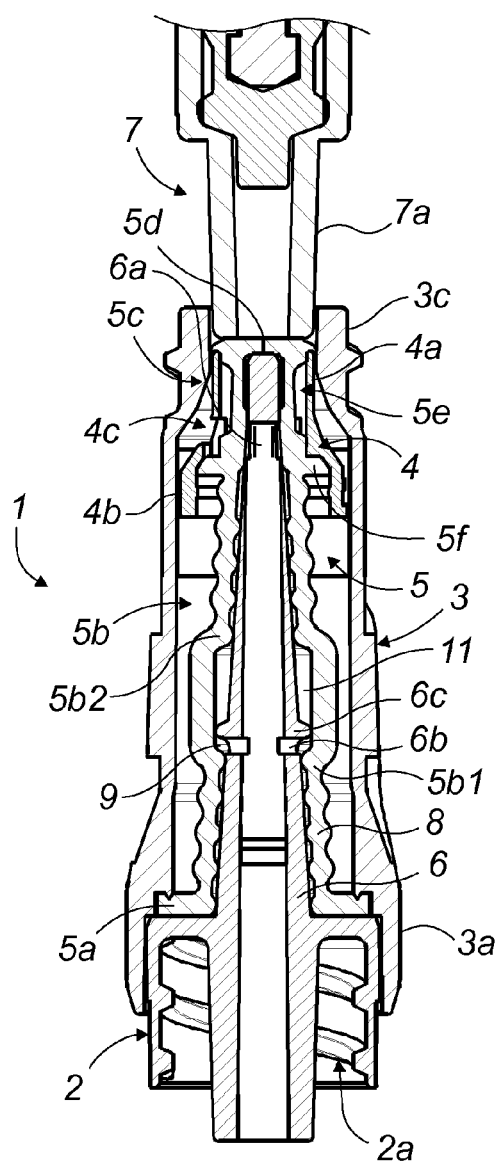
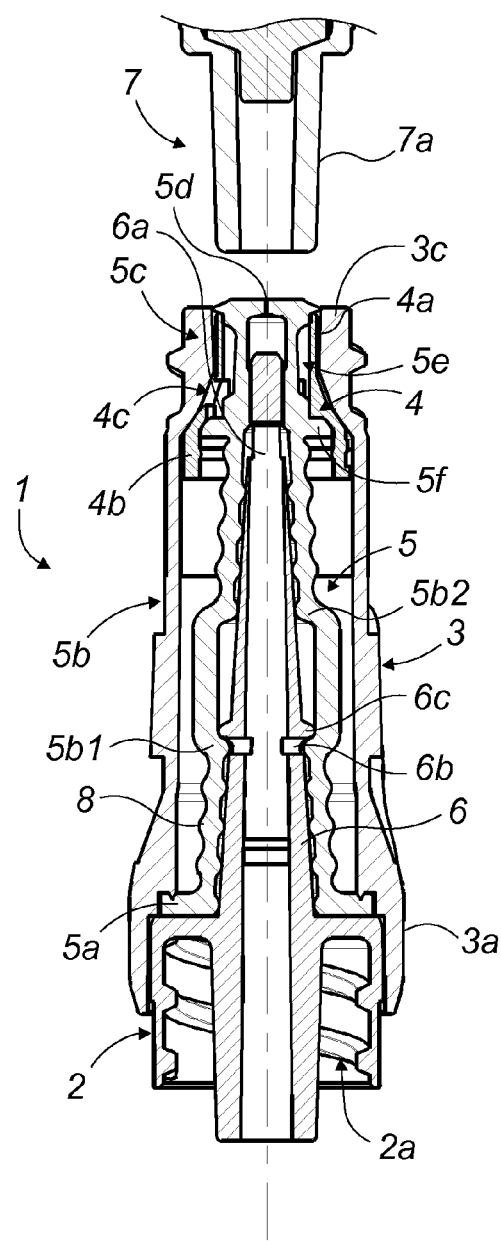

MEDICAL CONNECTOR

CROSS-REFERENCE TO RELATED APPLICATIONS

This application is a national stage application, and claims the benefit of priority, of International Patent Application No. PCT/FR2014/050153, filed Jan. 28, 2014, and entitled "Improved Medical Connector," which claims the benefit of priority of French patent application FR 1350836, filed Jan. 31, 2013, each of which is incorporated herein by reference in its entirety and for all purposes.

TECHNICAL FIELD

This description relates to the technical field of medical connectors, and more particularly relates to a medical connector that comprises a chamber supported by a joint, provided with a needle for dispensing a fluid; the needle is sheathed with a resilient seal.

BACKGROUND

The document EP 1 890 760 describes a medical connector with a first end known as the "upstream end", intended to be connected to a catheter connected to a patient; and a second end, referred to as "downstream end", intended to be interlinked with a device for sampling or injection of liquids through a male luer connector. In this document, reference is made to the terms "upstream end" and "downstream end" regardless of the direction of the flow of liquid.

In practice, this connector has a chamber supported at its base by a connector constituting the upstream end of the connector itself. The free end of the chamber, opposite the base, is intended for receiving, by friction, the tip of a male luer connector. The passage of the liquid between the catheter connected to the upstream end of the connector and the end of the male luer is ensured through a needle secured by the body of the joint. The needle extends to the chamber and opens into the terminal end of said chamber.

The needle is sheathed and maintained in the cavity of a resilient seal that has, in the thickness of its free terminal end, a slit or a similar opening allowing the needle to pass through when the resilient seal is compressed in the connected position vis à vis the connector.

In practice, this type of connector is used both for blood sampling and the injection of parenteral bags. In both cases, once the operation is completed, the catheter is cleaned with saline or alcohol.

However, the connector described above, which produces adequate results, can be improved.

The return of the resilient seal to its original position upon disconnection from the connector causes negative pressure at the terminal end of the needle. This phenomenon thus generates a suction of liquid present in the catheter, and leads at the same time to the pumping of the patient's blood to the base of the catheter, which causes obvious hygiene problems. The catheter clogs and creates a biofilm that might be infected.

To solve this problem, the document WO2008/052140 describes a connector whose needle has two longitudinal slits in which, when not connected, protrusions on the inner wall of the resilient seal are created. Insofar as these protrusions are only formed on part of the circumference of the seal, the liquid from the uncovered slits flows from both sides of the slits, in the upstream as well as the downstream direction. In other words, during connection, the entire volume between the barrel of the needle and the inner wall of the resilient seal is filled with liquid. Given the presence of flanges over the entire height of the resilient seal, a residual volume of liquid between the flanges on either side of the lateral holes will remain in the disconnected position. This stagnant fluid cannot be purged to the extent that the holes are clogged after disconnection. As a result, there is an obvious risk of contamination.

The document WO2006/013433A1 describes a similar connector except that the lateral holes are never closed. As previously described, because of the shape of the resilient seal, a residual volume of liquid remains between the wall of the seal and that of the needle after disconnection.

SUMMARY OF THE DISCLOSURE

The purpose of the presently described embodiments is to remedy the aforementioned disadvantages by providing a medical connector that does not cause any undesirable liquid recovery when disconnected and that leaves little to no residual volume (preferably the latter).

The objective of the presently described embodiments is to provide a connector capable of generating, upon disconnection, a pressure for returning a volume of liquid in the needle which is at least equal to the additional volume of liquid pumped from the catheter. More generally, the volume returned corresponds to the volume pumped (neutral valve). In this case, the catheter is entirely filled with the injected liquid. Or the returned volume is slightly higher than the volume pumped out (positive valve). In the latter case, a small volume of injected liquid enters the patient's vein.

To achieve this objective, a medical connector was developed. This connector comprises a joint fixed to a chamber, the connector being provided at its centre with a needle extending into the said chamber and opening into its terminal end, which has a section suitable for receiving, by friction, a male luer connector for the circulation of a fluid; the needle has a distal portion with at least one lateral hole opening into and contained in a cavity of a resilient seal that has, in the thickness of its free end, a slit or similar opening. The resilient seal is compressed when connected to uncover the distal portion of the needle and ensure the transfer of fluid, and released when disconnected.

The connector is characterised in that the needle has, apart from its distal portion, at least one additional hole. It is further characterised in that the resilient seal and the needle are shaped so that:

when the connector is connected, the resilient seal in the compressed state forms, in conjunction with the needle and immediately upstream of the upper level of the additional hole and only on the portion of the distance separating the said hole of the upstream end from the seal, a sealed cavity for receiving, by way of passage through the additional hole, a part of the fluid contained in the needle, when the resilient seal goes from the compressed state to the released state:

the cavity still contains fluid when at least one lateral hole opening into the needle is sealed by the resilient seal, the portions of the resilient seal, downstream and upstream of the cavity respectively, and the additional hole are shaped so that the downstream portion of the resilient seal closes at least one lateral hole while the same cavity continues to discharge the fluid contained therein into the needle.

In the description and in the claims, the term "distal end of the needle" refers to the portion of the needle that is not covered by the resilient seal in the connected position of the connector.

Similarly, the term "connected" means that liquid can pass between the male luer and the needle.

Furthermore, "a resilient seal in the compressed state forms, in conjunction with the needle, immediately upstream of the upper level of the additional hole and only on the portion of the distance separating the said hole of the upstream end from the seal" means that the sealed cavity does not extend upstream of the upper level of the additional hole over the entire length of the needle, but only over part of it. This means that the hole is contained within the sealed cavity in the connected position and that the liquid cannot flow between the wall of the resilient seal and the barrel of the needle on either side of the cavity thus delimited.

According to an essential characteristic, the cavity is present in the connected position of the connector, regardless of whether it exists or not before connection.

When there is no cavity before connection, it is formed immediately upstream of the upper level of the said additional hole; the volume of the cavity increases progressively with the compression of the resilient seal over a portion of the length thereof. When there is a cavity before connection, it moves along the needle, as a result of the compression of the resilient seal, in a direction upstream of the device.

In an advantageous form of embodiment:
when the connector is not connected, at least one additional hole is closed by the resilient seal,
when the connector is connected, at least one additional hole is not closed by the resilient seal.

Consequently and in practice, when connected, the resilient seal is compressed under the effect of the force exerted by the terminal end of the male luer connector which is inserted into the terminal end of the chamber. This compression causes the release of the additional hole and immediately forms, upstream of the next upper level (in the direction of flow), a sealed clearance volume between the inner wall of the seal and the wall of the needle; this is formed only along the distance separating the additional hole in the base from the joint or the needle. Part of the fluid flowing in the needle is drawn through the additional hole into the cavity thus formed. After disconnection, the seal gradually returns to its original position by spring force. This release leads to the pumping of the fluid present in the cavity by the scraping of the lower edge of the cavity along the barrel of the needle and the reintroduction of the entire volume in the barrel of the needle through the additional hole. According to an essential characteristic, when the resilient seal moves from the compressed state to the released state, the cavity still contains fluid until the open hole of the needle is sealed by the resilient seal. To do this, the portions of the resilient seal, downstream and upstream of the cavity respectively, as well as the additional hole, are shaped so that the downstream portion of the resilient seal closes the lateral hole while the same cavity continues to discharge the fluid contained therein into the needle. In these conditions, a certain volume of fluid is pumped back to the needle intended to compensate for the depression created at the terminal end of the needle during disconnection, thus preventing unwanted pumping of fluid and/or blood from the catheter. In practice, during disconnection, the portion of the resilient seal downstream of the additional holes rises along the needle faster than the upstream portion. In particular, the reintroduction of liquid into the barrel of the needle through the additional hole, depending on its size, creates resistance and prevents the seal from rising. After the manipulation, the sealed cavity contains almost no liquid as per the tolerances of manufacture of the resilient seal.

According to the presently described embodiments, the additional hole is formed on the barrel of the needle, preferably in its middle section.

According to a first form of embodiment of the connector (in disconnected position):
the resilient seal has on its inner wall a peripheral pad adapted to close at least one additional hole,
immediately downstream of the hole, for at least part of the distance separating the said hole from the distal end of the needle, the needle and the inner wall of the seal are of a complementary shape,
immediately upstream of the additional hole, the needle and the inner wall of the seal do not have a complementary shape.

In other words, the cavity is only formed during connection, by compression of the resilient seal. The portion of the seal in contact with the needle downstream of the hole moves linearly upstream. When the additional hole is freed, a space is created between the wall of the seal and the barrel of the needle which is at this level, in a shape that does not complement the shape of the inner wall of the resilient seal.

In a preferred form of embodiment, the needle and the inner wall of the seal are of a complementary shape for only part of the distance separating the said hole from the distal end of the needle.

To ensure the formation of the cavity upstream of the additional hole during seal compression, the wall of the part of the seal whose shape complements that of the needle is stiffer than that of the rest of the seal. Therefore, the portion of the resilient seal in contact with the needle undergoes a linear movement under the effect of the force exerted by the connector during connection, resulting in the formation of the cavity upstream of the additional hole.

Advantageously,
the inner wall of the resilient seal has a generally conical shape over its entire length,
immediately upstream of the additional hole, the needle has a cylindrical outer section.

In a particular form of embodiment, immediately upstream of the additional hole, the needle has a first part with a cylindrical outer section and a second conical part with an outer section that increases towards the base of the needle.

Advantageously, the outer section of the second part at its origin is greater than the outer section of the first section, so as to form a peripheral edge for support and an end position of the peripheral pad adapted to close at least one additional hole when the resilient seal is in the compressed position, thus ensuring that the chamber is sealed.

In a second form of embodiment, the resilient seal has a preformed cavity before connection.

More specifically and in this case preferably (disconnected position of the connector):
the resilient seal has on its inner wall a first peripheral pad adapted to close at least one additional hole,
immediately downstream of the additional hole, on at least part of the distance separating the said hole from the distal end of the needle, the needle and the inner wall of the seal are of a non-complementary shape and demarcate a rigid, sealed cavity,
immediately downstream of the additional orifice, the needle has a peripheral edge with a section identical or almost identical to that of the cavity.

Advantageously, immediately downstream of the peripheral pad, the inner wall of the seal has a tubular portion demarcated downstream by a second peripheral pad held in tight contact with the needle when the seal is in the released position.

In this case, during connection, the preformed cavity moves linearly upstream relative to the needle. When the hole is uncovered, the cavity fills with fluid. Due to the presence of the peripheral edge, the wall of the cavity is in tight contact with the said edge, so that the cavity formed below the upper level of the additional hole fills with liquid and remains sealed. The peripheral edge serves as a support and an end position to in second peripheral pad when the resilient seal is in the compressed position. When the seal returns to its initial position, the cavity empties itself by undergoing the same linear movement but in a downstream direction, without the liquid flowing between the elastic wall and the barrel of the needle beyond the peripheral edge. As before, in these conditions, no liquid remains in the cavity after disconnection.

According to another characteristic, the wall of the tubular portion is more rigid than the rest of the seal. Advantageously, the tubular portion of the seal is grooved.

As already stated, in all forms of embodiment, to ensure that the cavity continues to discharge the fluid in the needle when the open hole of the needle is closed by the resilient seal, the portions of the elastic seal, downstream and upstream of the cavity respectively, as well as the additional hole, are shaped in such a way that when the seal goes from the compressed state to the released state, the downstream portion of the elastic seal rises faster than the upstream portion. To do this, it is necessary to find a compromise between the elasticity of the portion of the seal upstream of the cavity and the one located downstream of the said cavity, while considering the size of the hole which acts as additional resistance when the fluid goes back into the needle.

In a preferred form of embodiment, the wall of the seal upstream and downstream of the cavity is in the form of a succession of pads, giving the parts of the seal identical rigidity downstream and upstream of the cavity.

The number of additional holes is not limited provided that their positioning is compatible with the operation of the connector.

In practice, there are two additional holes which are positioned opposite one another.

BRIEF DESCRIPTION OF THE DRAWINGS

The presently described embodiments will be better understood and other characteristics and advantages of the presently described embodiments will become clearer from the description that is given below—which is provided for information purposes only and is in no way exhaustive—with reference to the enclosed drawings, wherein:

FIGS. 2 to 10 are schematic representations of the longitudinal section of the connector according to the presently described embodiments and a first form of embodiment.

FIGS. 11 to 15 are schematic representations of the longitudinal section of the connector according to the presently described embodiments and a second form of embodiment.

DETAILED DESCRIPTION

Figure 1:
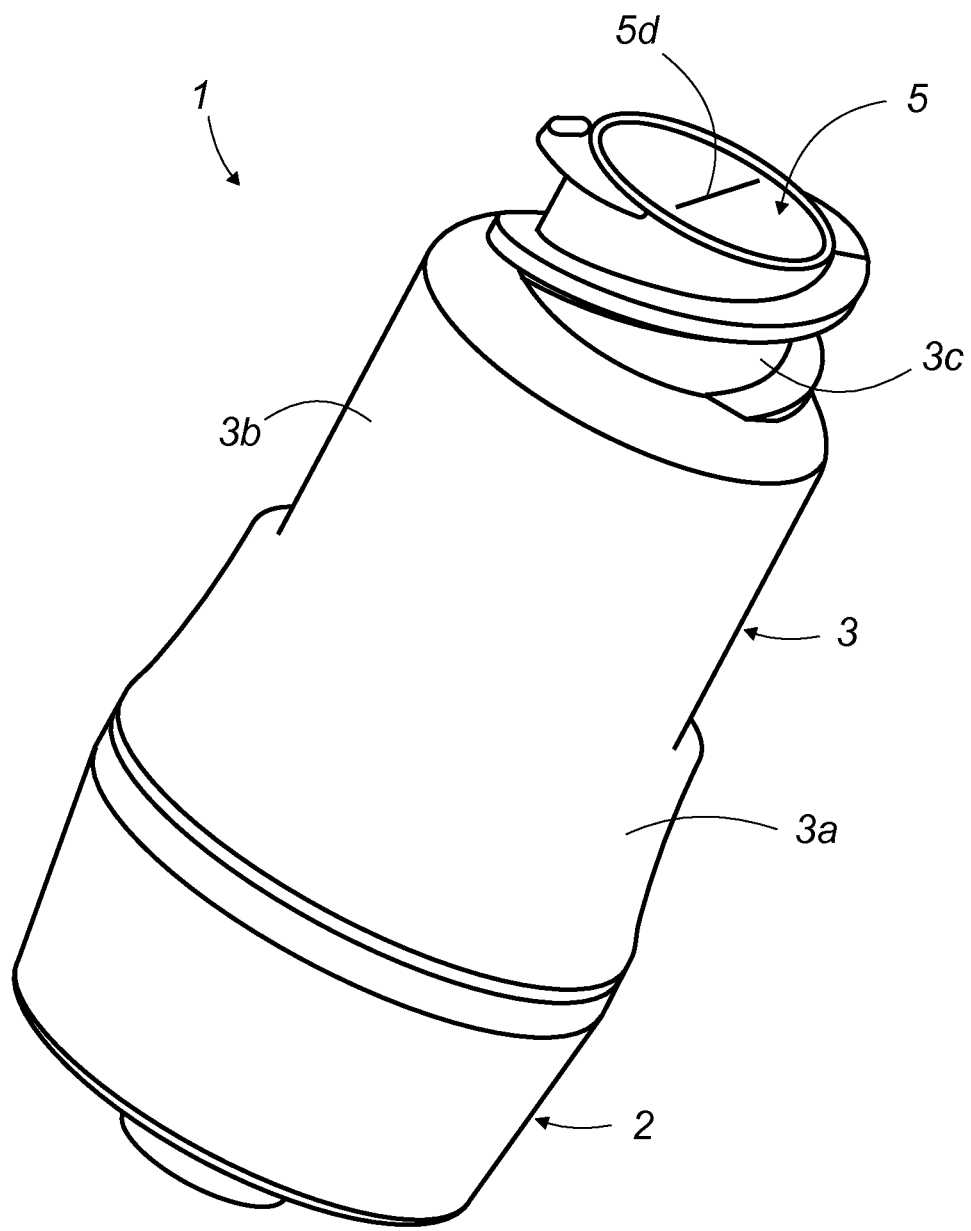
FIG. 1 is a perspective schematic representation of a medical connector in accordance with the presently described embodiments.
Figure 8:
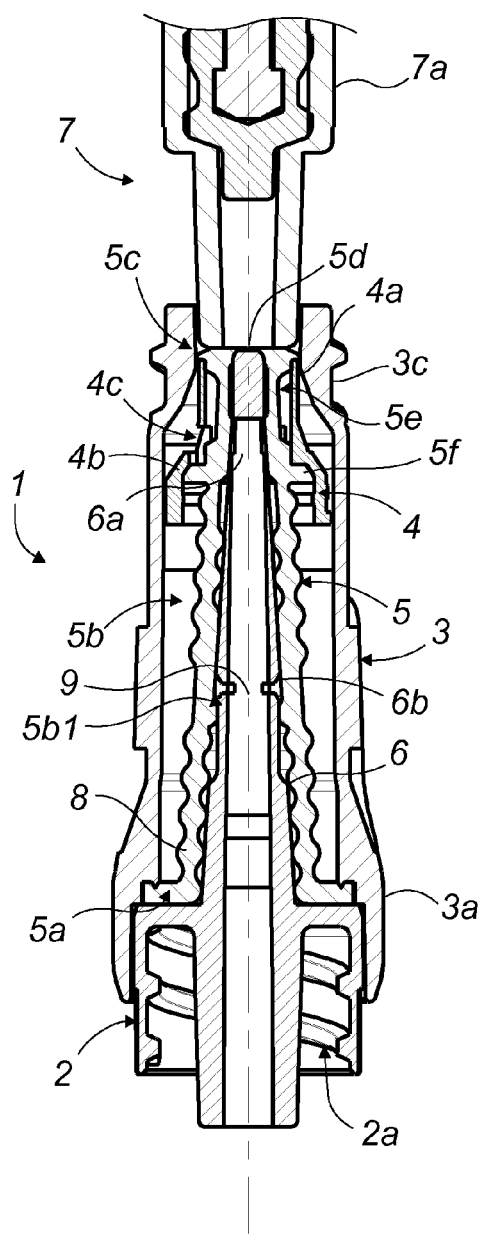
Figure 9:
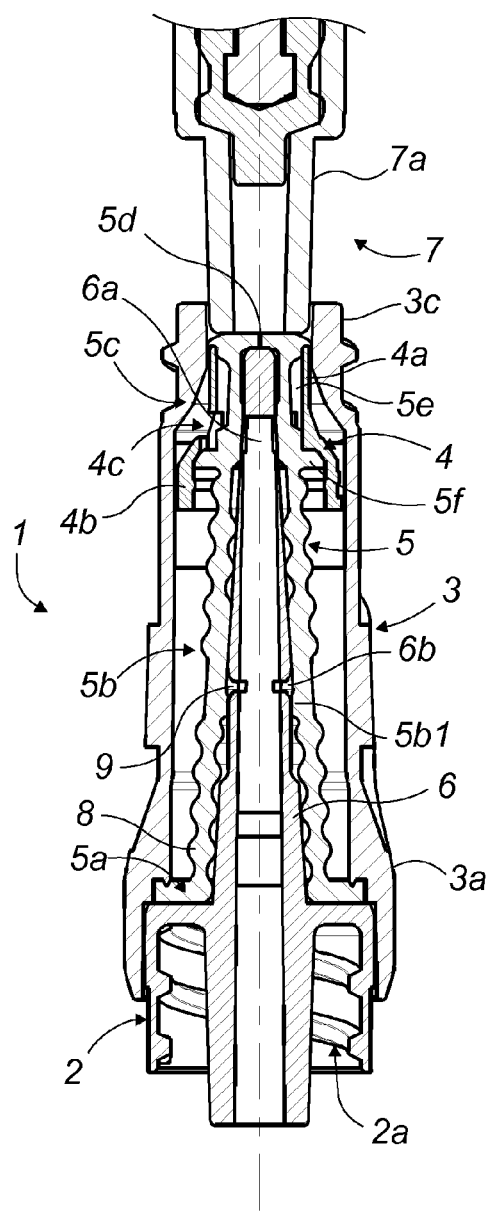
Figure 12:
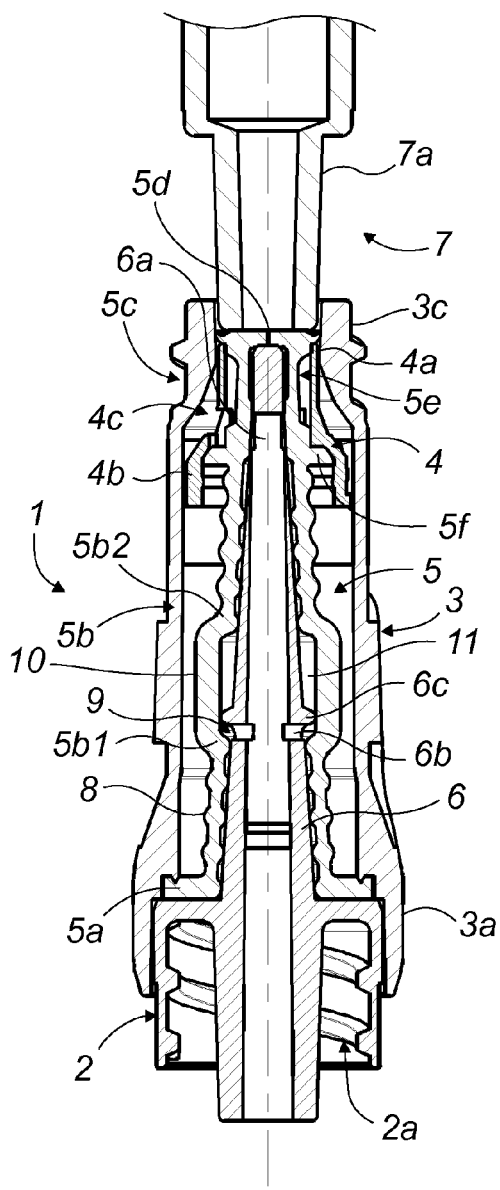

With particular reference to FIG. 1, which shows a medical connector (1) according to the presently described embodiments, the connector comprises a joint (2) fixed to a chamber (3) and a ring assembly (4)/resilient seal (5). The joint (2) is in the form of a composite part combining the body of the joint (2) itself and a needle (6). The chamber (3) comprises a proximal compartment (3a), a central compartment (3b) and a distal compartment (3c).

The distal compartment (3c) of the chamber (3) has a section capable of receiving, by friction, a male luer connector (7). The proximal compartment (3a) of the chamber (3) operates with the joint (2) which is intended for receiving a catheter connecting the patient and in which a fluid circulates.

As shown in FIGS. 2 to 15, the body of the joint (2) comprises a recess (2a), provided on its inner side with a screw thread intended to operate with a corresponding screw thread of a catheter or another female luer connector in which a fluid can flow. The body of the joint (2) is provided at its centre with a needle (6) extending from the proximal compartment (3a) to the distal compartment (3c).

The needle (6) itself is provided, close to its free end, which is itself closed, with two upper lateral holes (6a) through which the fluid flows when its distal portion is uncovered, that is to say in the connected position. The entire length of the needle (6) is sheathed in the cavity of a resilient seal (5) whose terminal portion is encircled by a ring (4). The distal end of at least the needle (6) has a substantially conical shape so as to facilitate its release under the effect of the thrust exerted by the male luer connector (7) on the ring assembly (4)/resilient seal (5).

According to the presently described embodiments, the needle (6) comprises two additional holes on the lower side (6b), located in its middle part. They are diametrically opposite one another.

In the form of embodiment shown in FIGS. 2 to 10, the needle has a conical section (6c) downstream of the orifices (6b). Upstream of the orifices (6b), the needle has a first part (6d) with a cylindrical outer section and a second part (6e) with a conical outer section increasing towards the base of the needle. Originally, the second part had a greater diameter than the first part so as to form a peripheral edge (6f).

The resilient seal (5) is made of silicone and is in the form of a tube with an outer section that is conical in shape, intended to extend into the chamber (3) from the body of the joint (2) up to the free end of the terminal compartment (3c) of the chamber (3). The seal (5) comprises a base portion (5a), a middle portion (5b) and an end portion (5c).

The base portion (5a) of the resilient seal (5) is intended to rest on the body of the joint (2). In a non-compressed position, that is to say in the released position, neither the base portion (5a) of the resilient seal (5) nor the central portion (5b) is in contact with the walls of the chamber (3).

The inner wall of the middle portion (5b) of the resilient seal (5) comprises a peripheral pad (5b1) positioned so as to close the lower lateral holes (6b) of the needle when the seal is in the released position, that is to say when disconnected.

Directly downstream of this pad, the inner wall of the seal has a conical shape (5b2) complementary to that of the needle with which it is in contact The outer side of the seal at this level is rectilinear and more rigid than the rest of the seal. The rigidity can be enhanced by providing longitudinal grooves on the corresponding seal portion. Downstream of the said rectilinear zone (5b2), the wall of the resilient seal (5b3) up to the distal end comprises a succession of pads. Similarly, in its portion (5b4) located upstream of the peripheral pad (5b1), the wall of the seal comprises a succession of pads up to its upstream end.

The kinematics of the resilient seal during connection and disconnection are as follows.

As shown in FIGS. 3 to 5, under the effect of the pressure exerted by the male luer on the resilient seal, the portion downstream of the lower pad (5b1) is compressed more rapidly than the upstream portion. Thus, the lower pad (5b1) undergoes a linear movement over a very short distance, making it possible to release the additional holes (6b). At the same time, the downstream part is subjected to linear movement over a greater distance, thereby gradually releasing the distal end from the needle. As shown in FIG. 6, the linear movement of the lower pad (5b1) results in its displacement up to the peripheral edge (6f) of the needle (6). A sealed clearance volume (9), delimited by the cylindrical wall of the needle (6d), the inner wall (5b2) of the middle portion (5b) of the resilient seal (5) and the said pad (5b1), is formed simultaneously and filled with the liquid flowing in the needle. The seal ends its travel when the pad (5b1) acts as a support for the peripheral edge (6f). At the same time, the portion of the resilient seal downstream of the additional holes is sufficiently compressed to uncover the upper lateral holes (6a). The liquid can then flow from the male luer connector into the needle of the invented connector.

When the resilient seal (5) returns to the released position, the lower pad (5b1) gradually rises and forces the liquid present in the sealed clearance volume (9) inside the needle (6) through the lower lateral holes (6b). The kinematics of the resilient seal (FIGS. 7-9) is the same as that found during compression (FIGS. 3-5), but in reverse. As shown in FIG. 10) the lower pad (5b1) returns to its original position, that is to say, to the position wherein the lower lateral holes (6b) of the needle (6) are closed. According to the presently described embodiments, to ensure these specific kinematics, the volume of the cavity, the elastic characteristics of the parts 5b3 and 5b4 of the joint as well as the size of the additional holes are calculated so that part 5b3 of the joint downstream of the cavity rises faster than the upstream part of the cavity. Therefore, the cavity does not empty completely before the open holes of the needle are fully closed by the disconnected seal. The reinjection of the contents of the cavity into the barrel of the needle when the seal returns to its rest position thus compensates for the rise of liquid, particularly blood, generated by the disconnection in the tubing.

In a second form of embodiment, shown in FIGS. 11 to 15, the resilient seal comprises a preformed cavity.

In this form of embodiment, the resilient seal still has on its inner wall a peripheral pad (5b1) referred to as in this case as the "first pad", which is capable of closing the two additional holes (6b).

Immediately downstream of the first peripheral pad (5b1), the inner wall of the seal has a tubular portion (10) demarcated downstream by a second peripheral bead (5b2) held in tight contact with the needle. The assembly thus forms a cavity (11) whose wall (10) is stiffer than the rest of the seal.

Also in this second form of embodiment, the needle has, directly downstream of the additional hole, a peripheral edge (6c) for the support and end position of the second peripheral pad (5b2) in the compressed position of the resilient seal. This pad (6c) helps to provide the clearance volume with (9) optimum sealing in the connected position. It also acts as a stop for the lower pad (5b1) in the released position of the resilient seal (5). In this way, the liquid can flow downstream of the peripheral edge (6c) in the downstream direction, between the elastic wall and the barrel of the needle.

As before, the volume of the cavity, the elastic characteristics of the parts of the joint upstream and downstream of the cavity, and the size of the additional holes are calculated so that the part of the joint downstream of the cavity rises faster than the upstream part of the cavity.

In practice, during the compression of the resilient seal (5), that is to say when connecting to a male luer connector (7), the cavity (11) undergoes a linear movement in a direction upstream of the connector. The lower pad (5b1) thus uncovers the holes (6c), so that the cavity is gradually filled with the fluid circulating in the barrel of the needle. The cavity ends its course when the second peripheral pad (5b2) acts as a support for the peripheral edge of the needle (6c).

When the resilient seal (5) returns to an initial position by spring force, the lower pad (5b1) rises and forces the liquid, by way of scraping, inside the needle (6) through the lower lateral holes (6b), until the said lower pad (5b1) returns to its original position, thus sealing the lower lateral holes (6b) of the needle (6). Before the lower lateral holes are closed, the part of the seal downstream of the cavity has already closed the open holes of the needle. As already mentioned, the volume of liquid is confined within the portion of the cavity located upstream of the additional hole and cannot flow beyond the peripheral edge (6b), regardless of whether the device is connected or disconnected.

The volume of liquid thus reintroduced into the barrel of the needle creates pressure in order to compensate for the depression created by the disconnection at the terminal part of the needle (6) and thus prevent any risk of an undesirable rise of.

In the connector (1) according to the presently described embodiments, regardless of the form of embodiment, the terminal part (5c) of the resilient seal (5) is further provided with a slit (5d), allowing the passage of the needle (6) when the resilient seal (5) is in a "compressed" position. The terminal part (5c) of the resilient seal (5) further comprises a recess (5e) upstream of the end of the needle (6) when the resilient seal (5) is in a compressed position. The terminal part (5c) also has a collar (5f), which allows the guiding and centring of the said terminal part (5c) of the resilient seal (5) in the central compartment (3b) of the chamber (3). To take into consideration the shape and dimensions of the central compartment (3b) of the chamber (3), this collar (5f) is also encircled by the ring (4).

The ring (4) is positioned at the end of the resilient seal (5) and has two parts with different sections: a first cylindrical part (4a) encircling the terminal portion (5c) of the resilient seal (5) over a length corresponding to the length of the terminal compartment (3c) and with a section that is substantially equal to the section of the said terminal compartment (3c), and a second cylindrical part (4b) with a substantially larger section equal to the corresponding section of the central compartment (3b) and covering the collar (5f) of the resilient seal (5). The ring (4) is made of a rigid or semi-rigid material, possibly using two materials with the resilient seal (5), or separately, the ring (4) and seal (5) are fixed to one another by bonding or simple apposition. The outer section of the seal (5) is substantially equal to the inner section of the ring (4) on their overlap area.

As shown in FIGS. 2 to 15, the terminal part and more particularly the first cylindrical portion (4a) of the ring (4) has two openworks (4c) designed to promote the delivery of the plastic material during the passage of the needle (6) under the effect of the pressure created by the installation of the male luer connector (7).

The central compartment (3b) and the terminal compartment (3c) are connected by a shoulder serving as a stop for the ring (4) encircling the terminal end (5c) of the resilient seal (5) in the rest position, i.e. when the seal is in the released position.

Figure 13:
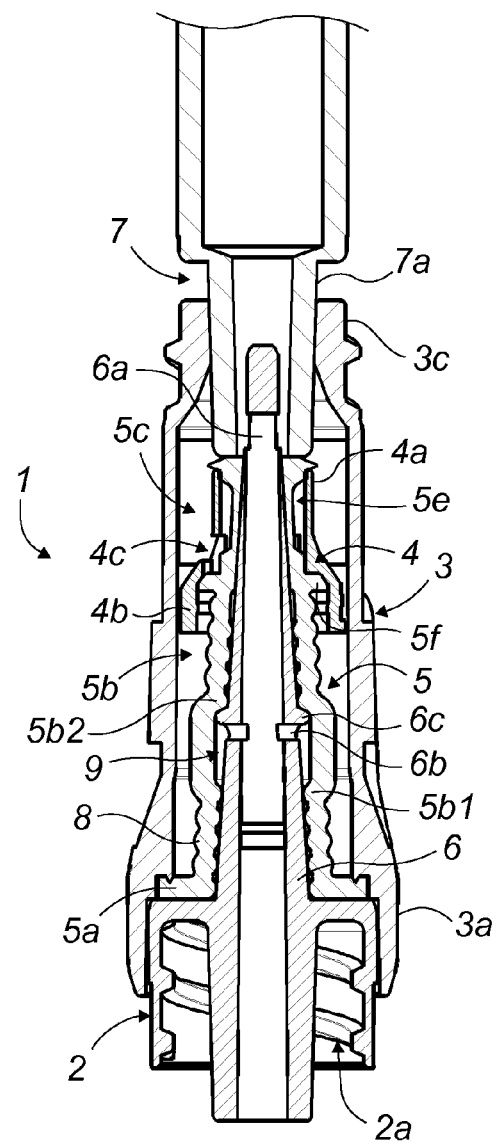

The connected position is more accurately depicted in FIGS. 6 and 13 by the installation of a male luer connector (7). This connector (7) is further provided with a luer cone (7a), to be inserted into the light of the compartment of the terminal (3c) of the chamber (3). In practice, the cone (7a) takes support using its end from the free end of the ring assembly (4)/resilient seal (5). This support causes movement of the resilient seal (5) along the barrel of the needle (6) towards the joint (2) and then the passage of the tip of the needle (6) through the slit (5d), facilitated by the recesses (5e), and finally the release of the lateral upper holes (6a), thus allowing passage of the fluid.

In the connected position, the distal end of the needle (6) is thus in its entirety, contained in the inner channel of the cone (7a), thus allowing the transmission of fluid from connector (1) to connector (7). The movement of the ring (4) during this operation is a homogeneous and uniform axial movement with permanent contact of the walls of the ring (4) section with the central compartment (3b) of the chamber (3) throughout the movement, with minimum friction.

As apparent from the foregoing, the present disclosure provides a medical connector (1) that provides entirely satisfactory use. Of particular note is the compensation of the undesired rise of the fluid due to disconnection of the connector (1).

The invention claimed is:

1. A medical connector comprising a joint fixed to a chamber, the joint being provided at a center of the medical connector with a needle extending into said chamber and opening into a terminal end of the medical connector, which has a section suitable for receiving, by friction, a male luer connector for the circulation of a fluid; the needle has a distal portion with at least one lateral hole opening into and contained in a cavity of a resilient seal having, in the thickness of a free end of the seal, a slit, the resilient seal being compressed when connected to uncover the distal portion of the needle and ensure the transfer of fluid, and released when disconnected, wherein the needle has, apart from the distal portion of the needle, at least one additional hole and wherein the resilient seal and the needle are shaped so that:

when the connector is connected, the resilient seal in the compressed state forms with the needle, immediately upstream of an upper level of the additional hole in the direction of an upstream end of the seal and only on a portion of the distance separating the additional hole from the upstream end of the seal, a sealed cavity for receiving by way of passage in the additional hole a part of the fluid contained in the needle, and when the resilient seal goes from the compressed state to the released state:

the sealed cavity still contains fluid when the at least one lateral hole opening into the needle is sealed by the portion of the resilient seal downstream of the sealed cavity, the portions of the resilient seal, downstream and upstream of the sealed cavity respectively, as well as the additional hole are shaped so that the portion downstream of the sealed cavity closes at least one lateral hole while the sealed cavity continues to discharge the fluid contained therein into the needle through the at least the additional hole.

2. A connector according to claim 1, wherein the additional hole is formed in the middle portion of the needle.

3. A connector according to claim 1, wherein:

when the connector is not connected, at least one additional hole is closed by the resilient seal, when the connector is connected, at least one additional hole is not closed by the resilient seal.

4. A connector according to claim 3, wherein:

the resilient seal has on its inner wall a peripheral pad adapted to close at least one additional hole, immediately downstream of the additional hole, on at least part of the distance separating said hole from the distal end of the needle, the needle and the inner wall of the seal are of complementary shape, immediately upstream of the additional hole, the needle and the inner wall of the seal do not have a complementary shape.

5. A connector according to claim 4, wherein the needle and the inner wall of the seal are of complementary shape on only part of the distance separating said hole from the distal portion of the needle.

6. A connector according to claim 4, wherein the inner wall of the part of the seal complimentary in shape to the needle is stiffer than that of the rest of the seal.

7. A connector according to claim 4, wherein:

the inner wall of the resilient seal has a generally conical shape over its entire length, immediately upstream of the additional hole, the needle has a cylindrical outer section.

8. A connector according to claim 7, wherein immediately upstream of the additional hole, the needle has a first part with a cylindrical outer section and a second conical part with an outer section that increases towards the base of the needle.

9. A connector according to claim 3, wherein:

the resilient seal has on its inner wall a first peripheral pad adapted to close at least one additional hole, immediately downstream of the additional hole, on at least part of the distance separating said hole from the distal portion of the needle, the needle and the inner wall of the seal are of non-complementary shape and demarcate a rigid, sealed cavity, immediately downstream of the additional orifice, the needle has a peripheral edge with a section substantially identical or almost identical to that of the cavity.

10. A connector according to claim 9, wherein immediately downstream of the first peripheral pad, the inner wall of the seal has a tubular portion demarcated downstream by a second peripheral bead held in tight contact with the needle.

11. A connector according to claim 9, wherein the wall of a tubular portion of the seal is more rigid than the rest of the seal.

12. A connector according to claim 1, wherein the wall of the seal upstream and downstream of the cavity is in the form of a succession of pads giving the parts of the seal identical rigidity downstream and upstream of the cavity.

13. A connector according to claim 1, wherein the at least one additional hole comprises at least two additional holes.

* * * * *